United States Patent [19]
Kalidindi

[11] Patent Number: 5,583,304
[45] Date of Patent: Dec. 10, 1996

[54] APPARATUS AND METHOD FOR TESTING POWDER PROPERTIES

[76] Inventor: Sanyasi R. Kalidindi, 8303 Hana Rd., Edison, N.J. 08817

[21] Appl. No.: 535,482

[22] Filed: Sep. 28, 1995

[51] Int. Cl.$^6$ .................................................. G01N 1/00
[52] U.S. Cl. ........................... 73/863.56; 73/865.6
[58] Field of Search ............................ 73/866, 865.6, 73/865.8, 662, 663, 863.01, 863.21, 863.52, 863.56, 863.57, 863.86, 864.33

[56] References Cited

U.S. PATENT DOCUMENTS

| | | | |
|---|---|---|---|
| 2,496,632 | 2/1950 | Lazan | 73/67 |
| 3,015,949 | 1/1962 | Arnold | 73/71.5 |
| 3,690,179 | 9/1972 | Olson | 73/863.56 |
| 4,043,756 | 8/1977 | Sommervold | 23/230 R |
| 4,061,019 | 12/1977 | Blasetti | 73/662 |
| 4,248,315 | 2/1981 | Falinower | 177/50 |
| 4,715,229 | 12/1987 | Butts | 73/663 |
| 4,718,288 | 1/1988 | Leschonski et al. | 73/863.52 |
| 4,849,175 | 7/1989 | Dupain et al. | 422/63 |
| 4,951,511 | 8/1990 | Perron et al. | 73/863.56 |
| 5,220,825 | 6/1993 | Peterson et al. | 73/863.01 |
| 5,224,635 | 7/1993 | Wise | 222/608 |

FOREIGN PATENT DOCUMENTS

| | | | |
|---|---|---|---|
| 58-67330 | 4/1983 | Japan | 366/108 |
| 965494 | 10/1982 | U.S.S.R. | 366/108 |
| 1353605 | 5/1974 | United Kingdom | 73/863.56 |

*Primary Examiner*—Robert Raevis
*Attorney, Agent, or Firm*—Richard C. Litman

[57] ABSTRACT

An apparatus and method for studying powder segregation and flow properties using research and development size batches in order to be able to predict segregation and flow problems in production batches. The apparatus and method subject the powder in a hopper to frequencies of vibration usually experienced in a typical production environment and automatically collect unit-dose samples at the bottom of the hopper stem at predetermined sampling intervals. The apparatus and method allow such testing to be done on either a static bed of powder or a dynamic bed of powder, and permit manual sampling from different locations in the powder bed in addition to the samples automatically taken at the bottom of the hopper stem.

19 Claims, 2 Drawing Sheets

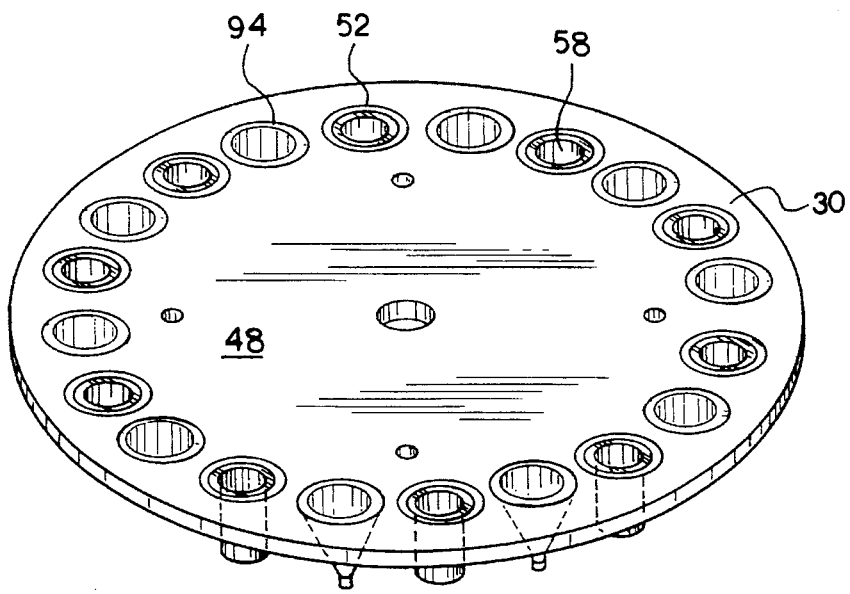
FIG. 2
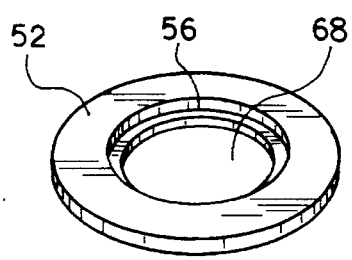
FIG. 3
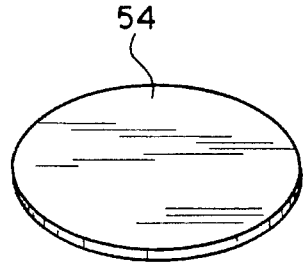
FIG. 4
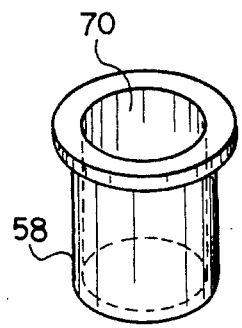
FIG. 5
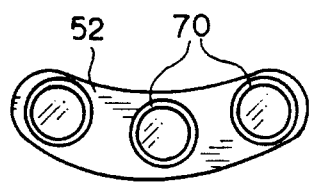
FIG. 8
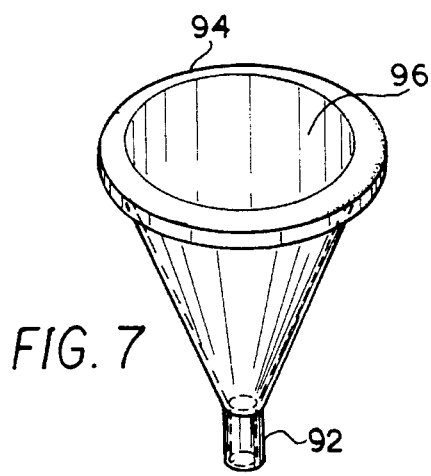
FIG. 7
FIG. 6

APPARATUS AND METHOD FOR TESTING POWDER PROPERTIES

BACKGROUND OF THE INVENTION

1. Field of the Invention

The present invention provides the apparatus and methods for studying the segregation and flowing properties of pharmaceutical powders at a research and development level, under static and dynamic conditions of the powder bed, mimicking the real production environment in a pilot plant operation, and predicting segregation and flow problems in production scale batches.

Many of the pharmaceutical and food dosage forms are made by mixing different powders prior to further processing such as compression into tablets, filling into capsules, filling into bottles or pouches, etc. Such further processing usually leads to potential segregation of the ingredients, unless the correct ingredients are chosen based on particle size and bulk density. Segregation leads to problems in powder homogeneity and requirements for content uniformity. Presently, segregation in powder blends is studied at both the research and development level and at the production level by obtaining samples of the final product, e.g., tablets or capsules, at different time intervals throughout the processing run and analyzing the samples for content uniformity. However, segregation is a time-dependent variable, i.e., the longer the processing run, the worse the segregation becomes. Therefore, such quality control studies on small research and development batches do not provide a true production picture because of the short processing run time. Although such studies on production size batches provide a meaningful picture, the problem exists that it is neither practical nor economical to experiment with large production size batches.

Thus, the present invention provides an apparatus for studying powder segregation and flow properties using research and development size batches under simulated conditions of production size batches. First, in order to simulate the vibration and mechanical shaking in a production environment, the present invention incorporates an adjustable frequency vibration device which facilitates the study under different frequency levels of vibration. Secondly, this apparatus incorporates a microprocessor with time control to study powder segregation for prolonged time periods and to take samples at programmed time intervals automatically. Thirdly, this invention incorporates a carousel system, rotated by an electric motor, with dies to collect unit-dose samples of the powder blend, i.e., a sample size equal to one dose of the final product such as a tablet or a capsule, such dies being replaceable to suit each product under study. Fourthly, this apparatus will also facilitate segregation studies under both static bed and dynamic bed conditions, i.e., simulating a powder blend stored in a tote bag in a warehouse (static bed) and a powder blend flowing from a hopper into a machine (dynamic bed). Fifthly, this apparatus will also help determine the flow rates of powders at different levels of vibration using funnel-shaped devices with stems having different bore sizes.

2. Description of the Prior Art

The prior art has not considered the necessity of a powder segregation and flow testing apparatus and the method of using such an apparatus to study the properties of powder segregation and flow on small research and development size batches under simulated production conditions in order to make such tests both scientifically meaningful and economical.

A number of patents have been issued that address vibration testing of various materials. These patents will be discussed in the order of their perceived relevance to the claimed invention.

In Japanese Patent No. 67330 issued on Apr. 21, 1983 to Koei Sangyo K. K., an apparatus for mixing, crushing or separating different pharmaceutical powders is described. The tank is vibrated on a base with coil springs and by a vibrator having weights fixed to eccentric locations of a rotary shaft. Agglomeration of the mixing powder is prevented by injecting gas. No disclosure of a carousel to collect samples is evident.

In Soviet Patent No. 965,494 issued on Oct. 15, 1982 to Yu A. Brodskii, a continuous powder mixer and three-compartment blender for processing pharmaceutical material, inter alia, is described. An eccentric weight vibrator and flexible support shock absorbers are also disclosed. Carousel collection of samples is not disclosed.

In U.S. Pat. No. 5,224,635 issued on Jul. 6, 1993 to Thomas W. Wise, a mobile pharmaceutical hopper containing two hoppers with one inside the other is described. Capsules, tablets and powders are stored in this hopper. No agitation means is disclosed.

In U.S. Pat. No. 4,043,756 issued on Aug. 23, 1977 to David E. Sommervold, an automatic chemical calibrating and testing apparatus which includes a carousel is described. Sample containers containing chemical samples and blanks are tested by a computer. There is no disclosure wherein a powder is dispensed from a hopper while the sample table is rotated.

In U.S. Pat. No. 4,849,175 issued on Jul. 18, 1989 to Jean R. Dupain et al., an apparatus for automatically determining certain characteristics of cement by utilizing swiveling arms which rotate to various peripheral stations is described.

In U.S. Pat. No. 4,248,315 issued on Feb. 3, 1981 to Charles Falinower, a feed-mechanism A and a weighing device P for the volumetric analysis of cement powder is described. The feed-mechanism includes an arrangement of a funnel feeding powder to two silos which empties the powder onto separate revolving trays which feed the powder to a hopper and a vibrating chute which transfers the powder to weighing device P. Weighing device P rotates to carry the sample to be weighed by an arm to a weighing station. No rotating table containing sample containers is disclosed.

Various vibration devices are disclosed in U.S. Pat. No. 2,496,632 issued on Feb. 7, 1950 to Benjamin J. Lazan; U.S. Pat. No. 3,015,949 issued on Jan. 9, 1962 to Howard H. Arnold; U.S. Pat. No. 4,061,019 issued on Dec. 6, 1977 to David H. Blasetti; and U.S. Pat. No. 4,715,229 issued on Dec. 29, 1987 to Gary Butts.

These disclosures are hereby incorporated by reference as to various conventional apparatuses which may not be fully disclosed in this disclosure.

None of the above inventions and patents, taken either singly or in combination, is seen to describe the instant invention as claimed.

SUMMARY OF THE INVENTION

Accordingly, it is a principal object of the invention to provide an apparatus for testing segregation potential and flow of a powder blend on a small batch size under simulated production conditions in order to be able to predict the segregation potential in a large production size batch.

It is another object of the invention to provide an apparatus with a single or dual hopper system to feed the material to a rotating carousel containing dies while subjecting the powder to a predetermined degree of vibration.

It is a further object of the invention to provide an apparatus and method for automatically collecting either a single unit-dose sample or multiple unit-dose samples using interchangeable die inserts of different volumes at predetermined time intervals.

It is another object of the invention to provide an apparatus and method to determine flow rates of powder samples under different conditions of vibration frequency and time periods.

Still another object of the invention is to provide an apparatus and a method to test under static and dynamic conditions.

It is an object of the invention to provide improved elements and arrangements thereof in an apparatus and method for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2 is an isometric assembly view of the carousel plate having apertures filled with die holders holding dies alternating with funnels.

FIG. 3 is an isometric view of a die holder.

FIG. 4 is an isometric view of an aperture cover.

FIG. 5 is an isometric view of a die or cup.

FIG. 6 is an assembly view of a spring-loaded butterfly valve in open and closed positions inside the funnel stem and manipulable with an outside handle.

FIG. 7 is an isometric view of a funnel as shown in FIG. 2 for determining the segregation and flow properties of a powder sample under dynamic conditions.

FIG. 8 is a top view of a curved die holder with three sampling dies.

Similar reference characters denote corresponding features consistently throughout the attached drawings.

DETAILED DESCRIPTION OF THE PREFERRED EMBODIMENTS

Figure 1:
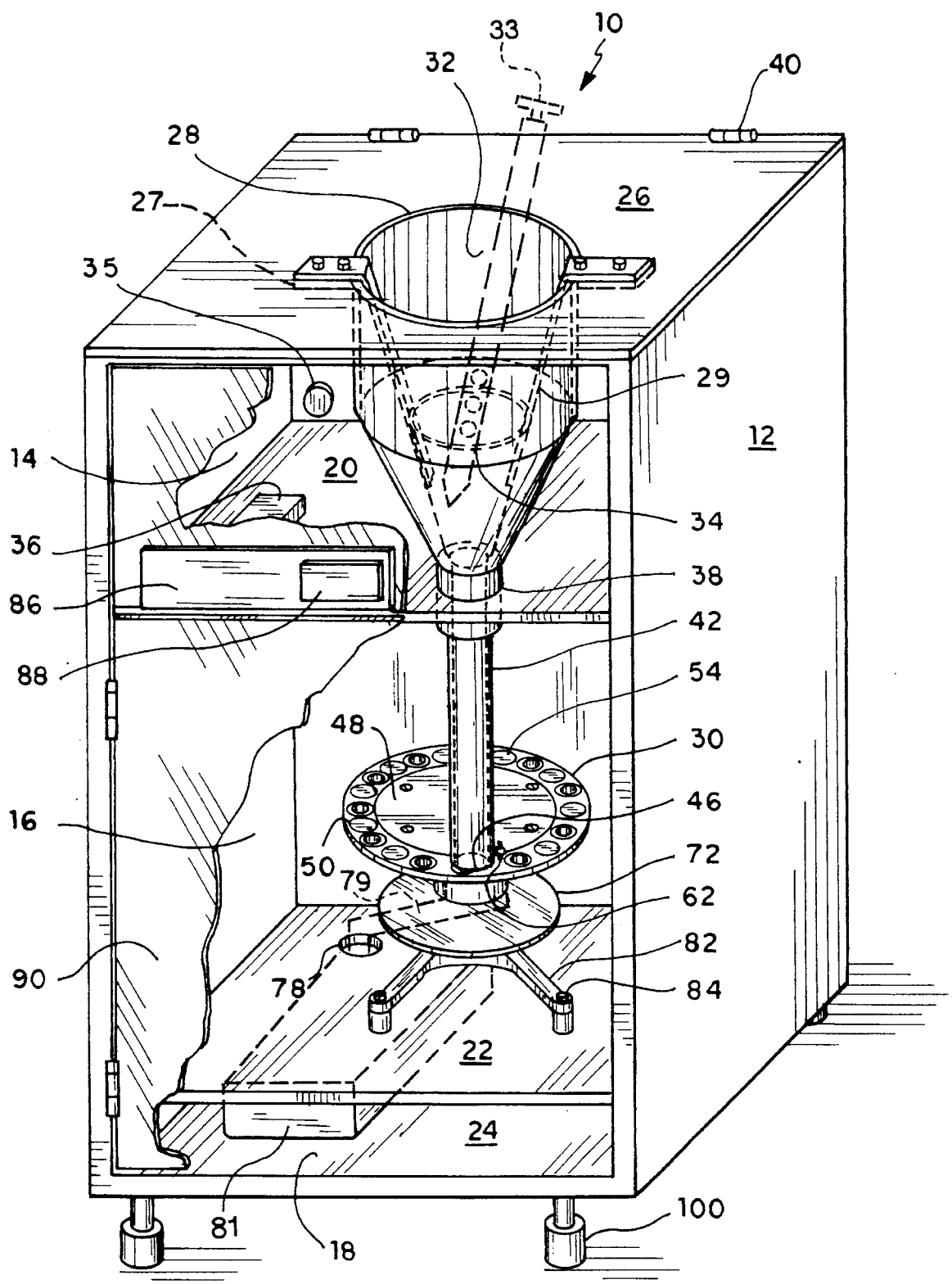
FIG. 1 is an isometric assembly view with a partial breakaway of the front panels of the segregation and flow testing apparatus with the carousel plate containing sampling dies alternating with covered apertures.

FIG. 1 illustrates the powder testing apparatus 10 which is a rectangular sided housing 12 having three compartments 14 (top), 16 (middle) and 18 (bottom). Alternatively, a cylindrical housing can be utilized in order to minimize the collection of extraneous powder inside a housing containing corners. The entire apparatus can be constructed of plastic and/or metal such as stainless steel or aluminum. A metal apparatus is preferred because of greater weight and minimization of excessive vibration. The top compartment 14 houses the upper (or outer) hopper 32, an adjustable frequency vibration device 35, and other electronic components 36. The top panel 26 of housing 12 has a first aperture 28 located off-center to align the vertical hopper system with one of the die holders located on the peripheral edge of carousel plate 30. The unique vertically positioned funnel-shaped hopper system consists of a long outer hopper 32 extending to the carousel plate 30 and an inner hopper 34 nesting within hopper 32 for allowing the powder properties to be studied when there is only a small amount of powder available for the study. The outer hopper 32 is anchored to the top panel 26 by means of two L-shaped brackets 27 wherein the upper end is removably fastened to the top panel 26 and the lower end is welded to the outside of the outer hopper 32. The optional conical inner hopper 34, when used, is anchored to the top panel 26 by means of extended and substantially L-shaped brackets 29 over brackets 27. The outer hopper 32 will be used alone if a large amount of powder is available for the study. The outer hopper 32 will be used in conjunction with the inner hopper 34 if only a small amount of powder is available for the study. The brackets 27 and 29 keep the hoppers from moving out of place while the system is vibrating. Outer hopper 32 has a stem 42 which passes through a second aperture 38 of floor 20. The inner hopper 34 has no stem of its own, but its bottom opening is of the same diameter as the diameter of the stem 42 of the outer hopper 32. The inside of the top compartment 14 can be accessed by opening the top panel 26 which is on hinges 40. Alternatively, the top panel 26 can be secured on its edges without hinges in order to enable the lifting out of the hopper unit and panel 26 as one unit.

In the middle compartment 16, the distal portion 46 of stem 42 abuts the top surface 48 of carousel plate 30 and overlies a series of equidistantly spaced third apertures 50 (FIG. 2) having stepped inside edges 56 (not shown) which can alternatively be elongated grooves or connected apertures (not shown) which hold die or cup holders 52 (FIG. 3) or blank covers 54 (FIG. 4). The die holders 52 have a stepped inside edge 56 to hold either one or more lipped multiple dies or cups 58 (FIGS. 5 and 8). The carousel plate 30 with its dies and die holders must necessarily be uniformly flat. Returning to stem 42, its distal portion 46 can further contain an attachment consisting of a butterfly valve 62 (which is kept in the open position with a spring means 64, FIG. 6) for cutting off the powder flow by handle 66 in the event the sampling trial is terminated with powder still remaining in the hopper.

The thin metal or plastic carousel plate 30 has as an example up to 20 of third apertures 50 located equidistantly from each other on its periphery. The utilization of different carousel plates containing a fewer number of apertures having larger diameters to accommodate larger die holders 52 and dies 58 for obtaining larger volume samples is contemplated. Within every alternate third aperture 50 is placed a plastic die holder 52 (FIG. 3) having a fourth aperture 68 for insertion of circular metal, e.g., stainless steel, or plastic dies or cups 58 (FIG. 5), having a cavity 70 of a predetermined variable volume for obtaining unit-dose powder samples. As noted above, the fourth aperture 68 is not limited to a circular hole, but can be in the form of a groove to accommodate several dies 58 in order to obtain several samples simultaneously at each sampling time interval as shown in FIG. 8, wherein 3 dies 58 in a holder 52 are illustrated. The sample sizes contemplated for pharmaceutical powder compositions are from 15 mg. to 200 gm. The sample sizes may vary in other industries. In each alternating vacant aperture 50, a blank cover 54 made from a metal or a plastic (FIG. 4) or a funnel die 94 made of plastic (FIG. 7), having a fifth aperture 96 on top and a sixth aperture 92 at the bottom of the stem is positioned. Therefore, dies 58 and blank covers 54 (or funnel dies 94 in FIG. 2) are situated in alternate positions around the periphery of the carousel plate 30 as depicted in FIG. 1. Each funnel 94 in FIG. 7 has an aperture 96 of a predetermined diameter and an aperture 92 of the neck or stem portion of a predetermined diameter.

Returning to FIG. 1, the carousel plate 30 is attached to a commercially available turntable 72 which is driven by an electric impulse motor which is not shown since it is inside the turntable housing. The legs 82 of turntable 72 are anchored to the surface or floor 22 by threaded bolts 84 which adjust the legs 82 for leveling the turntable 72. The level of vibration, sampling intervals, duration of sampling, total test period, and the intermittent or continuous mode of sampling are all controlled by a microprocessor 86 with an incorporated timer and digital display 88. Continuous sampling is done automatically by feeding powder into the dies on the carousel plate 30. It is also contemplated that unit-dose samples may also be taken manually from the powder bed in the hoppers 32 and 34 using a unit-dose sampling device as described in U.S. Pat. No. 5,337,620 issued Aug. 16, 1994 to applicant and U.S. Pat. No. 5,440,941 issued Aug. 15, 1995 to applicant. The teachings of both patents are hereby incorporated herein by reference. The surface or floor 22 has a seventh aperture 78 into which may be inserted a funnel 79 to guide the powder flowing out of the covered funnel dies 94 having holes 96 of a specific size into a tray 81 resting on the surface or floor 24 in the bottom compartment 18. The carousel plate 30, the turntable 72 and the tray in the bottom compartment 18 are all accessed by opening the hinged access panel 90. The housing 12 is supported on four rubber legs 100 to prevent the apparatus 10 from moving during the sampling operation.

The method of studying powder properties using this apparatus 10 comprises the following illustrative example. The die holders 52 and the blank covers 54 (if the study is to be done on a static bed of powder) or the funnel dies 94 (if the study is to be done on a dynamic bed of powder) are inserted into alternate third apertures 50 on the carousel plate 30. The dies 58 of appropriate volume cavity 70 are inserted into the fourth apertures 68 of the die holders 52 and are nested on the edges 56. The carousel plate 30 is then placed on the turntable 72 and fastened. The outer hopper 32 or the combination of the outer hopper 32 and inner hopper 34 is inserted into the housing 12 through the first aperture 28 and second aperture 38, and the stem 42 is aligned with the first blank cover 54 or the first funnel die 94. The butterfly valve 62 is closed. The hopper system is fastened to the top panel 26 by means of either brackets 27 alone for the large hopper 32 or with brackets 29 of the inner hopper 34 when both hoppers are utilized. Powder is placed inside hopper 32 and/or 34. The apparatus 10 is energized. The test parameters, such as the level of vibration, the sampling interval, the duration of sampling, the mode of sampling (intermittent or continuous), and the total test period, are selected and programmed on the microprocessor 86. The test begins with the butterfly valve 62 being opened to let the powder flow. In the continuous mode of operation, the turntable 72 will rotate at a predetermined sampling interval to bring the first die 58 under the stem 42, stop there for a predetermined duration of sampling time and than move on to rest on the next blank cover 54 or the next funnel die 94. Thus, the powder fills the first die 58. This process will continue automatically until the turntable makes one complete turn, unless it is programmed to stop after a predetermined number of stations. In the intermittent mode of operation, the turntable 72 will rotate at a predetermined sampling interval to bring the first die 58 under the distal portion of stem 42 and wait there until further instruction is given by the programmed microprocessor to move on. During this waiting period, manual sampling may be done from the powder bed in the hopper 32 or 34 by using any of the unit-dose sampling devices described in my above mentioned U.S. Pat. Nos. 5,337,620 and 5,440,941. A powder sampler 33 in dashed outline is depicted in FIG. 1. Once the test is completed, the dies 58 are removed from the carousel plate 30, and the samples are analyzed for content uniformity and tested for physical properties.

When the funnel dies 94 are used, the powdered material will be flowing out continuously through the sixth aperture 92 in the bottom of each funnel die 94 and is collected through the seventh aperture 78 into a tray in the bottom compartment 18. The flow rate of this powder may be determined by weighing the total quantity of powder that has passed through any one funnel die 94 in a given length of time. In both static and dynamic modes of operation, a large sample, instead of a unit-dose sample, can be collected at each sampling interval for determination of physical properties such as particle size distribution, bulk density and the like.

It is to be understood that the present invention is not limited to the sole embodiment described above, but encompasses any and all embodiments within the scope of the following claims.

I claim:

1. An apparatus for testing the physical properties of a powder sample including segregation and flow rates comprising:

a housing having a top surface containing a first aperture located proximate to an edge of said surface, said housing comprising a top compartment, an intermediate compartment and a bottom compartment, wherein the top compartment supports a first cylindrical hopper in said first aperture;

the intermediate compartment contains a centrally located carousel plate rotatable by a turntable, wherein said carousel plate contains a series of second apertures located around a periphery of said carousel and equidistantly spaced, said second apertures holding dies containing sampling cavities alternating with elements selected from blank covers and funnel dies;

said first cylindrical hopper for accepting a powder sample extending vertically from said first aperture to said carousel and having a first stem abutting said carousel;

a programmable vibration device located in said top compartment which causes vibration of the housing;

a timing device located in said top compartment to rotate said carousel in predetermined time intervals;

a drive mechanism attached to said carousel in said intermediate compartment to cause its rotation at predetermined intervals from one second aperture to another adjacent second aperture;

a microprocessor in said top compartment adapted to control said programmable vibration device, said timing device and said drive mechanism for a predetermined test sequence; and resilient footings beneath the housing which accommodate said vibration, whereby upon vibration of said housing by said vibration device, a powder sample is added to said first hopper, said powder sample descends to a die in said carousel, whereupon a segregated deposit of said powder sample is formed in the sampling cavity of said die over a predetermined time interval before the carousel is rotated to the next blank cover.

2. The apparatus according to claim 1, wherein said second apertures hold die holders which hold dies in their third apertures alternating with funnel dies.

3. The apparatus according to claim 2, wherein said funnel dies are positioned over a series of collection receptacles, wherein said accumulated powder can be further analyzed.

4. The apparatus according to claim 1, wherein said rotating carousel contains cavity-containing dies alternating with non-sampling covers.

5. The apparatus according to claim 1, wherein said vibration device mimics a production vibration frequency.

6. The apparatus according to claim 1, wherein each said second aperture contains a multiple die holder containing multiple dies with sampling cavities.

7. The apparatus according to claim 1, wherein said first cylindrical hopper is anchored to the housing by brackets.

8. The apparatus according to claim 1, wherein said first cylindrical hopper contains a closure element having a butterfly valve in its stem proximate to the carousel.

9. The apparatus according to claim 1, wherein said first conical hopper contains a second stemless cylindrical hopper, wherein a small quantity of a powder sample is analyzed.

10. The apparatus according to claim 9, wherein said second stemless conical hopper is fastened to said top surface of said apparatus by substantially L-shaped brackets.

11. A carousel assembly for testing the physical properties of a powder sample including segregation and flow rates comprising:

a thin flat circular plate containing a predetermined number of first apertures spaced equidistantly apart and proximate to the periphery of said circular plate;

sampling dies positioned within half of said predetermined number of first apertures alternating with an element selected from a funnel die having an aperture of a predetermined diameter and a neck portion of a predetermined diameter and a non-sampling cover;

rotating means for rotating said plate at a specific rate and at predetermined time intervals;

an adjustable frequency vibration means which simulates the vibration and mechanical shaking in a production environment to vibrate said flat circular plate and said dies; and a microprocessor adapted to control said rotating means and vibration means, whereby a powder is deposited into each said cavity and each selected said funnel die under vibration.

12. A carousel according to claim 11, wherein each said sampling die consists of a multiple die holder containing multiple dies with each die having a sampling cavity.

13. A carousel assembly according to claim 11, wherein each of said sampling dies positioned within half of said predetermined number of first apertures alternate with a funnel die having an aperture of a predetermined diameter and a neck portion of a predetermined diameter.

14. A carousel assembly according to claim 11, wherein each of said sampling dies positioned within half of said predetermined number of first apertures alternate with a non-sampling cover.

15. A method of testing the physical properties of a powder sample comprising:

adding a powder sample to a first hopper which is under a predetermined vibration frequency and which extends to and abuts the top surface of a carousel;

collecting the powder in a static bed for a predetermined duration of time by the first of a series of cavity-containing dies positioned in a die holder located at a periphery of said carousel;

rotating the carousel at predetermined intervals to collect further samples;

controlling the predetermined vibration frequency to mimic a production frequency and the predetermined rotation of said carousel by a microprocessor; and manually sampling the powder in the first hopper from above by a separate sampling device during non-collection, whereby over a predetermined period of time, samples of the powder are collected at regular intervals for examination of the static bed properties of each sample collected in said sampling cavities and in said first hopper.

16. A method according to claim 15, wherein each said sampling die holder contains multiple dies, and wherein each die contains a sampling cavity, whereby multiple static bed samples of the powder are taken at one deposition.

17. A method according to claim 15, wherein the carousel contains non-sampling blank covers alternating with cavity-containing dies.

18. A method according to claim 15, wherein in said rotating carousel, each sampling die alternates with a funnel die having an aperture of a predetermined diameter and a neck portion of a predetermined diameter, whereby a dynamic bed study is implemented by said funnel dies.

19. A method according to claim 15, wherein a second stemless hopper is inserted within the first hopper, whereby a small quantity of powder can be analyzed.

* * * * *